United States Patent [19]

Masuko et al.

[11] Patent Number: 4,536,599

[45] Date of Patent: Aug. 20, 1985

[54] SYNTHESIS OF AMINE DERIVATIVES

[75] Inventors: Fujio Masuko, Ohita; Tadashi Katsura, Itami, both of Japan

[73] Assignee: Sumitomo Chemical Company, Limited, Osaka, Japan

[21] Appl. No.: 90,479

[22] Filed: Nov. 1, 1979

Related U.S. Application Data

[63] Continuation-in-part of Ser. No. 65,429, Aug. 10, 1979, abandoned.

[30] Foreign Application Priority Data

Aug. 22, 1978 [JP] Japan ............................ 53-102614
Aug. 30, 1978 [JP] Japan ............................ 53-106541

[51] Int. Cl.³ .................... C07C 102/00; C07C 87/28
[52] U.S. Cl. .................................... 564/124; 564/373
[58] Field of Search ............... 260/570.5 R; 564/124, 564/373

[56] References Cited

U.S. PATENT DOCUMENTS

| | | | |
|---|---|---|---|
| 3,594,401 | 7/1971 | Cavalla et al. | 260/570.5 X |
| 3,597,458 | 8/1971 | Nakamura et al. | 260/570.5 X |
| 3,657,440 | 4/1972 | Werner | 260/570.5 X |
| 3,707,515 | 12/1972 | Huebner | 260/570.9 X |
| 3,739,019 | 6/1973 | Ueda et al. | 260/570.5 X |
| 3,766,194 | 10/1973 | Huebner | 260/570.5 X |
| 4,082,749 | 4/1978 | Seeger et al. | 260/570.9 X |

OTHER PUBLICATIONS

Adams et al., "Organic Reactions", vol. III, pp. 268–269, 273–274, and 280–281, (1956).
Seiji et al., "Chemical Abstracts", vol. 70, Section No. 87346j (1969).
Meyer et al., "Chemical Abstracts", vol. 56, p. 5882f, (1962).
Asami, "Chemical Abstracts", vol. 56, p. 403g, (1962).

Primary Examiner—Robert V. Hines
Attorney, Agent, or Firm—Stevens, Davis, Miller & Mosher

[57] ABSTRACT

An amine of the formula,

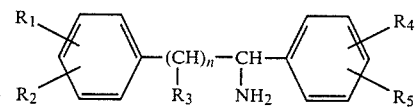

wherein $R_1$, $R_2$, $R_3$, $R_4$ and $R_5$ are each hydrogen, alkyl or the like and n is 1, 2 or 3, including α-phenyl-β-(p-tolyl)-ethylamine, which is useful as an optically resolving agent, an intermediate of medicines and the like, is effectively produced by a novel process comprising hydrolysis of the corresponding nitrile of the formula,

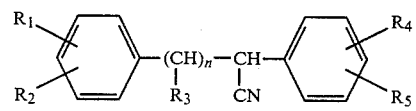

wherein $R_1$, $R_2$, $R_3$, $R_4$, $R_5$ and n are the same as above, followed by alkali-decomposition of the resulting amide of the formula,

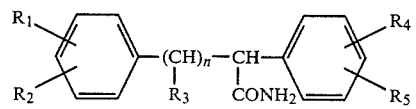

wherein $R_1$, $R_2$, $R_3$, $R_4$, $R_5$ and n are the same as above. An amide including the above one is effectively produced by hydrolysis of the corresponding nitrile in the presence of a base and hydrogen peroxide using an organic quaternary ammonium salt and/or a tertiary amine as a catalyst.

2 Claims, 1 Drawing Figure

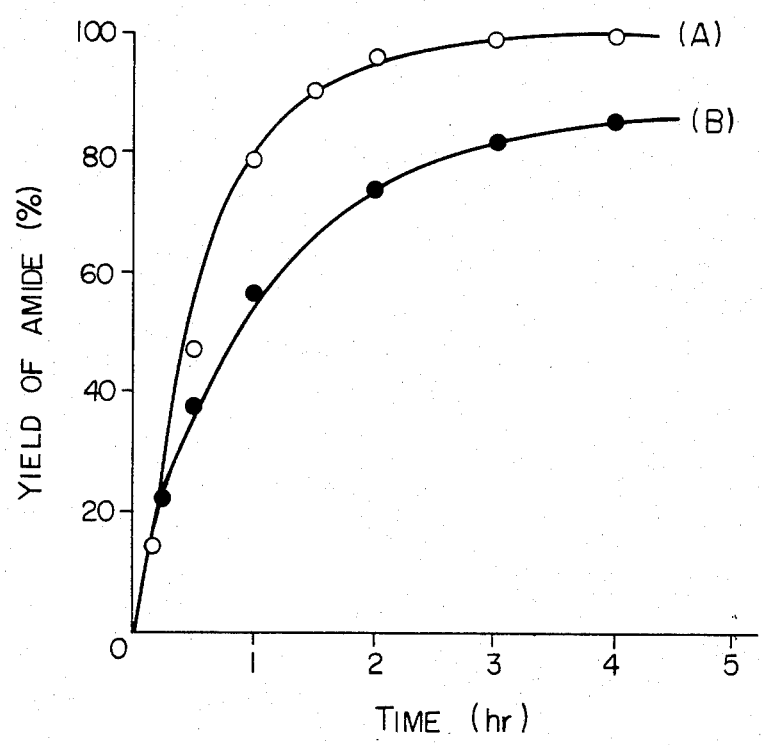

SYNTHESIS OF AMINE DERIVATIVES

This application is a continuation-in-part of the application, Ser. No. 65,429, filed Aug. 10, 1979, now abandoned.

This invention relates to novel processes for producing amide derivatives and amine derivatives.

More particularly, the invention relates to an improved process for producing an amide derivative of the formula (I), $$R-CONH_2 \quad (I)$$

wherein R represents a straight or branched $C_1$–$C_6$ alkyl or alkenyl group, or a phenyl or aralkyl group, provided that said alkyl or alkenyl group may further have a halogen atom, or an alkoxyl, alkylthio, dialkylamino, alkylsulfonyl, phenyl, phenoxy, phenylthio or hydroxy group, and said phenyl or aralkyl group may further have an alkyl, alkenyl, alkoxyl, alkylthio, dialkylamino, alkylsulfonyl, phenyl, phenoxy, phenylthio or hydroxy group, or a halogen atom.

The invention also relates to an improved process for producing an amine derivative of the formula (1),

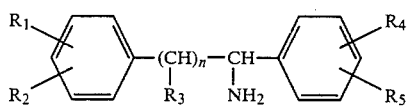

wherein $R_1$, $R_2$, $R_3$, $R_4$ and $R_5$ are independently hydrogen atom, a halogen atom, a hydroxy, trihalogenomethyl, phenyl, phenoxy or phenylthio group, or a straight or branched $C_1$–$C_6$ alkyl, alkenyl, alkoxyl, alkylthio, dialkylamino or alkylsulfonyl group, n is an integer of 1 to 3, provided that $R_3$s may be the same or different when n is 2 or 3, and either $R_1$ and $R_2$ or $R_4$ and $R_5$ may be bonded through the same or different atom.

The amide derivative of the formula (I) is important as an intermediate for medicines, agricultural chemicals, fine chemicals, dyestuffs or the like, and the amine derivative of the formula (1) is important as an optically resolving agent of medicines, agricultural chemicals or the like and also important as an intermediate of medicines having an excellent pharmacological effect such as anti-cholesterol effect or the like.

There has hitherto been known a process for producing the amide derivative of the formula (I), which comprises heating the corresponding nitrile compound with excess amount of hydrogen peroxide in an alcohol-water solvent in the presence of an alkali. However, this process is disadvantageously practiced in industry from the viewpoint of economy and danger for the reason that this process uses large amount of hydrogen peroxide.

A process for producing the amine derivative of the formula (1) shown in prior art will be discussed as follows taking as an example the compound wherein $R_1$ signifies 4-$CH_3$, $R_2$, $R_3$, $R_4$ and $R_5$ signify hydrogen atom and n signifies 1;

(A) In Compt. rend. vol. 240, 100 (1955), a method is shown, in which method the amine derivative is obtained by using the chloro-nitroso derivative as an intermediate and carrying out de-chlorination and reduction thereof using large amounts of nickel. However in this method, the synthesis of the said chloro-nitroso derivative is complicated and the further reduction step shows a low yield. Thus this method is not fit for industrial use.

(B) In Z. Physiol. Chem., vol. 289, 220 (1952), a method is shown, the method comprising condensing the expensive p-methylbenzaldehyde with nitrobenzyl to obtain nitro-methylstilbene as an intermediate and reducing the intermediate to obtain the amine derivative. However this method has not only a problem of raw material from an economical point of view, but also serious difficulties on adaptation for industrial practice owing to the explosiveness of nitrobenzyl, and further the method contains a problem on cost of equipment and safety of the process. Therefore this method cannot be adapted for industrial use.

(C) In Japanese Patent Publication No. 5330/1974, is disclosed a method which uses nitrobenzyl as raw material like method (B), and thus this method cannot be used for industrial practice owing to the explosiveness of the said compound.

(D) Another method is disclosed in Japanese Patent Publication No. 6311/1974. This method is carried out according to the following scheme:

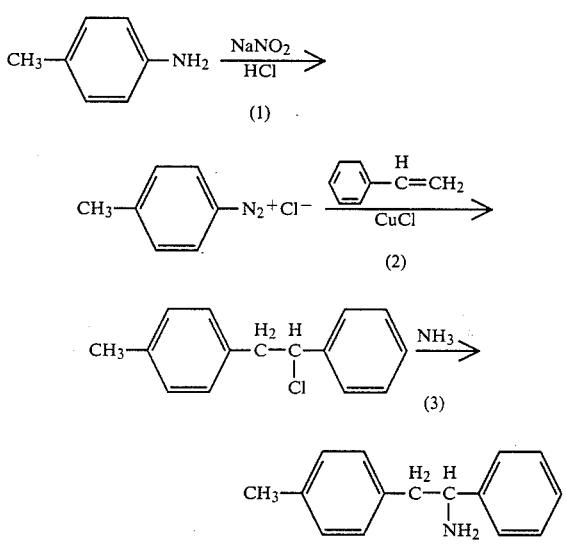

However, this method has defects as shown in the following:

(1) In the first step, the stability of diazonium salt is questionable.

(2) In the reaction of diazonium salt and olefin of the second step, Sandmeyer reaction occurs with the aimed Meerwein reaction and useless by-products are largely formed and thus this method generally shows a low yield.

(3) The third step is a reaction conducted in the presence of ammonia, and thus forms a large quantity of by-product and further contains a disadvantage regarding the apparatus to be used.

Under such circumstances, the present inventors have made an extensive investigation on hydrolysis of the nitrile to obtain the amide of the formula (I) and have found that the co-presence of an organic quaternary ammonium salt or tertiary amine in the said hydrolysis system produces from the industrial point of view prominent effects such that the amount of hydrogen peroxide used can largely be decreased and the reaction velocity becomes greater to permit the decrease of reaction time.

The inventors have further investigated to solve the problems mentioned above for obtaining the amine compound of the formula (1) and have found a very advantageous process. The present process using a reaction path quite different from the known methods, solves all of the defects brought about by the several kinds of synthetic methods in the prior art mentioned above, can give the desired product in a good yield and in a high purity and is easily put into industrial practice.

The present invention provides a process for preparing the amide compound of the formula (I)

$$R-CONH_2 \quad (I)$$

wherein R has the same meanings as above, which comprises hydrolyzing a nitrile compound of the formula (II)

$$R-CN \quad (II)$$

wherein R has the same meanings as above, in the presence of a base and hydrogen peroxide using an organic quaternary ammonium salt and/or tertiary amine as a catalyst.

The present invention further provides a process for preparing an amine derivative of the formula (1),

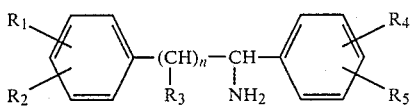

wherein $R_1$, $R_2$, $R_3$, $R_4$, $R_5$ and n have the same meanings as above, which comprises the steps of:
(1) obtaining a nitrile compound of the formula (3),

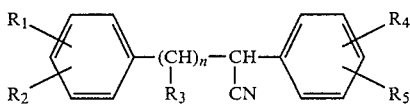

wherein $R_1$, $R_2$, $R_3$, $R_4$, $R_5$ and n have the same meanings as above, by condensing a compound of the formula (4),

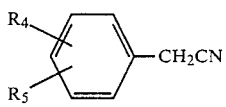

wherein $R_4$ and $R_5$ have the same meanings as above with a halogeno compound of the formula (5),

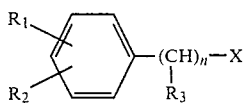

wherein $R_1$, $R_2$, $R_3$ and n have the same meanings as above, and X represents a halogen atom, in the presence of a base,
(2) obtaining a compound of the formula (2)

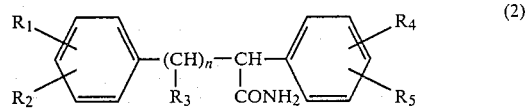

wherein $R_1$, $R_2$, $R_3$, $R_4$, $R_5$ and n have the same meanings as above, by hydrolyzing the compound of the formula (3), and
(3) obtaining the compound of the formula (1) by alkali-decomposing the compound of the formula (2).

In carrying out the process for producing the amide derivative of the formula (I), the compound of the formula (II) used as raw material in the present invention, includes, for example, acetonitrile, propionitrile, butyronitrile, isobutyronitrile, isopropenylnitrile, benzonitrile, acrylonitrile, 2- or 3-methoxypropionitrile, 2- or 3-phenoxypropionitrile, 2- or 3-phenylthiopropionitrile, 2- or 3-methylthiopropionitrile, 2- or 3-dimethylaminopropionitrile, 2- or 3-hydroxypropionitrile, 2- or 3-methylsulfonylpropionitrile, 2- or 3-chloropropionitrile, 2- or 3-bromopropionitrile, 2- or 3-phenylpropionitrile, 2- or 3-p-tolylpropionitrile, 2,3-dimethoxypropionitrile, 2,3-diphenoxypropionitrile, 2,3-bis(phenylthio)-propionitrile, 2,3-bis(methylthio)-propionitrile, 2,3-bis(-dimethylamino)-propionitrile, 2,3-bis(methylsulfonyl)-propionitrile, 2,3-dichloropropionitrile, 2,3-diphenylpropionitrile, 2-methoxy-3-ethoxypropionitrile, 2-phenoxy-3-phenylpropionitrile, 2-phenyl-3-(p-tolyl)-propionitrile, 2-phenyl-3-methylthiopropionitrile, 2-phenyl-3-hydroxypropionitrile, 2-chloro-3-bromopropionitrile, 2-methylsulfonyl-3-phenylpropionitrile, 3,3-diphenylpropionitrile, 3,3-diethoxypropionitrile, 3,3-bis(dimethylamino)-propionitrile, 2-phenyl-3,3-dichloropropionitrile, 2-(p-tolyl)-3,3-diphenylpropionitrile, 2,2-diphenyl-3-hydroxypropionitrile, 2,2,3-trichloropropionitrile, 2,3,3-triphenylpropionitrile, 2-phenyl-2-(p-tolyl)-3-chloropropionitrile, 2-phenylthioacetonitrile, 2,2-diphenylacetonitrile, 3-phenyl-4,4-dibromobutyronitrile, 2-phenyl-3-(p-tolyl)-acrylonitrile, 2,4-dichlorobenzonitrile and the like.

The hydrolysis is carried out in the presence or absence of a solvent. The solvents used for the reaction include, for example, water, alcohols such as methanol, ethanol, isopropanol, hexanol and butanols, t-butanols, benzene, toluene, xylene, chlorobenzenes, hexane, heptane, methyl cellosolve, dioxane, tetrahydrofuran, dimethylformamide, ether, dimethylsulfoxide and so on. These solvents are used alone, or in mixture. If the compound of the formula (II) is solid, it is preferred from an operational viewpoint to select a solvent capable of dissolving the compound of the formula (II).

As the base to be used, alkali metals, alkali metal hydroxides, alkali metal carbonates, alkali metal alkoxides, alkaline earth metal hydroxides, alkali metal hydrides etc. are illustrated. The amounts thereof to be used are arbitrarily selected from the range of 0.1 to 10 mols, preferably 0.1 to 2 mols per mol of the compound of the formula (II).

The amount of hydrogen peroxide to be used is arbitrarily in an amount over 1 mol, but it is sufficient in a range of about 2 to 3 mols per mol of the compound of the formula (II).

As the organic quaternary ammonium salt and tertiary amine to be used as catalyst, for example, tetra-n-butylammonium-chloride, -bromide or -hydroxide, tetraethylammonium-chloride, -bromide or -hydroxide, triethylbenzylammonium-chloride, -bromide or -hydroxide, triethylamine, trimethylamine, tributylamine, triisopropylamine, etc. are illustrated. These catalysts are used alone or in mixture. The amount of the catalyst to be used is arbitrarily selected in the range of 1/200 to 1/5 mol per mol of the raw compound of the formula (II), but is practically sufficient in an amount of about 1/100 mol per mol of the compound of the formula (II).

The reaction temperature is arbitrarily selected in the range of 0° to 300° C., preferably 20° C. to 100° C.

With regard to the reaction pressure, there is no limitation in particular, and atmospheric pressure or increased pressure is used as well.

The reaction is carried out well both in liquid or vapor phase, and in batch or continuous system.

After completion of the reaction, the reaction mixture can be subjected to conventional aftertreatment such as separation, concentration, distillation, crystallization, etc., whereby the desired compound of the formula (I) is obtained in good yield.

As the compound of the formula (I) thus obtained these are illustrated in the following; for example, acetamide, propionamide, butyramide, isobutyramide, isopropenylamide, benzamide, acrylamide, 2- or 3-methoxypropionamide, 2- or 3-phenoxypropionamide, 2- or 3-phenylthiopropionamide, 2- or 3-methylthiopropionamide, 2- or 3-dimethylaminopropionamide, 2- or 3-hydroxypropionamide, 2- or 3-methylsulfonylpropionamide, 2- or 3-chloropropionamide, 2- or 3-bromopropionamide, 2- or 3-phenylpropionamide, 2- or 3-p-tolylpropionamide, 2,3-dimethoxypropionamide, 2,3-diphenoxypropionamide, 2,3-bis(phenylthio)-propionamide, 2,3-bis(methylthio)-propionamide, 2,3-bis(dimethylamino)-propionamide, 2,3-bis(methylsulfonyl)-propionamide, 2,3-dichloropropionamide, 2,3-diphenylpropionamide, 2-methoxy-3-ethoxypropionamide, 2-phenoxy-3-phenylpropionamide, 2-phenyl-3-(p-tolyl)-propionamide, 2-phenyl-3-methyl-thiopropionamide, 2-phenyl-3-hydroxypropionamide, 2-chloro-3-bromopropionamide, 2-methylsulfonyl-3-phenylpropionamide, 3,3-diphenylpropionamide, 3,3-diethoxypropionamide, 3,3-bis(dimethylamino)-propionamide, 2-phenyl-3,3-dichloropropionamide, 2-(p-tolyl)-3,3-diphenylpropionamide, 2,2-diphenyl-3-hydroxypropionamide, 2,2,3-trichloropropionamide, 2,3,3-triphenylpropionamide, 2-phenyl-2-(p-tolyl)-3-chloropropionamide, 2-phenylthioacetamide, 2,2-diphenylacetamide, 3-phenyl-4,4-dibromobutyramide, 2-phenyl-3-(p-tolyl)-acrylamide, 2,4-dichlorobenzamide and the like.

As for the process for producing the amine derivative of the formula (1), a detailed explanation is given hereinafter.

The compound of the formula (3) is synthesized by the condensation reaction (step 1) of the compound of the formula (4) with the compound of the formula (5) in the presence of a base.

The compounds having the formula (5) used as raw material for step 1 are illustrated, for example, in the following.
Benzyl-chloride or -bromide,
o-, m- or p-chlorobenzyl-chloride or -bromide,
o-, m- or p-bromobenzyl-chloride or -bromide,
o-, m- or p-fluorobenzyl-chloride or -bromide,
o-, m- or p-methoxybenzyl-chloride or -bromide,
o-, m- or p-ethoxybenzyl-chloride or -bromide,
o-, m- or p-phenoxybenzyl-chloride or -bromide,
o-, m- or p-phenylthiobenzyl-chloride or -bromide,
o-, m- or p-methylthiobenzyl-chloride or -bromide,
o-, m- or p-dimethylaminobenzyl-chloride or -bromide,
o-, m- or p-methylsulfonylbenzyl-chloride or -bromide,
o-, m- or p-isopropenylbenzyl-chloride or -bromide,
o-, m- or p-methylbenzyl-chloride or -bromide,
o-, m- or p-ethylbenzyl-chloride or -bromide,
o-, m- or p-propylbenzyl-chloride or -bromide,
o-, m- or p-butylbenzyl-chloride or -bromide,
o-, m- or p-isopropylbenzyl-chloride or -bromide,
o-, m- or p-isobutylbenzyl-chloride or -bromide,
o-, m- or p-trichloromethylbenzyl-chloride or -bromide,
o-, m- or p-trifluoromethylbenzyl-chloride or -bromide,
o-, m- or p-hydroxymethylbenzyl-chloride or -bromide,
3,4-dimethoxybenzyl-chloride or -bromide,
3,4-dichlorobenzyl-chloride or -bromide,
3,5-dichlorobenzyl-chloride or -bromide,
2,4-dichlorobenzyl-chloride or -bromide,
3,4-dimethylbenzyl-chloride or -bromide,
2,5-dimethylbenzyl-chloride or -bromide,
2,4-dimethylbenzyl-chloride or -bromide,
3,4-methyleneoxybenzyl-chloride or -bromide,
3,4-dibromobenzyl-chloride or -bromide,
2,5-dibromobenzyl-chloride or -bromide,
2,4-dibromobenzyl-chloride or -bromide,
3,4-difluorobenzyl-chloride or -bromide,
2,5-difluorobenzyl-chloride or -bromide,
2,4-difluorobenzyl-chloride or -bromide,
o-, m- or p-methyl-α-methylbenzyl-chloride or -bromide,
o-, m- or p-methyl-α-methoxybenzyl-chloride or -bromide,
o-, m- or p-methylsulfonyl-α-methoxybenzylchloride or -bromide,
phenethyl-chloride or -bromide,
phenylpropyl-chloride and the like.

The compounds of the formula (4) are illustrated, for example, in the following.
benzylnitrile,
o-, m- or p-chlorobenzylnitrile,
o-, m- or p-bromobenzylnitrile,
o-, m- or p-fluorobenzylnitrile,
o-, m- or p-methoxybenzylnitrile,
o-, m- or p-ethoxybenzylnitrile,
o-, m- or p-phenoxybenzylnitrile,
o-, m- or p-phenylthiobenzylnitrile,
o-, m- or p-methylthiobenzylnitrile,
o-, m- or p-dimethylaminobenzylnitrile,
o-, m- or p-methylsulfonylbenzylnitrile,
o-, m- or p-isopropenylbenzylnitrile,
o-, m- or p-methylbenzylnitrile,
o-, m- or p-ethylbenzylnitrile,
o-, m- or p-propylbenzylnitrile,
o-, m- or p-butylbenzylnitrile,
o-, m- or p-isopropylbenzylnitrile,
o-, m- or p-isobutylbenzylnitrile,
o-, m- or p-trichloromethylbenzylnitrile,
o-, m- or p-trifluorobenzylnitrile,
o-, m- or p-hydroxybenzylnitrile,
3,4-dimethoxybenzylnitrile,
3,4-dichlorobenzylnitrile,
2,5-dichlorobenzylnitrile,
2,4-dichlorobenzylnitrile,
3,4-dimethylbenzylnitrile,
2,5-dimethylbenzylnitrile,
2,4-dimethylbenzylnitrile,
3,4-methyleneoxybenzylnitrile,
3,4-dibromobenzylnitrile,
2,5-dibromobenzylnitrile,
2,4-dibromobenzylnitrile, 3,4-difluorobenzylnitrile,
2,5-difluorobenzylnitrile,
2,4-difluorobenzylnitrile and the like.

In the reaction between the compounds of the formulas (4) and (5), the mol ratio of the compound of the formula (4) to the compound of the formula (5) is usually 1:0.1 to 1:3. in the case of using the compound of the formula (5) in an amount less than 1 mol per mol of the compound of the formula (4), the unreacted compound (4) acts as solvent and, after completion of the reaction, the compound of the formula (4) can be recovered from the reaction mixture by means of crystallization, distillation etc. and can be reused.

In the case of using the compound of the formula (5) in an amount more than 1 mole per mol of the compound of the formula (4), the unreacted compound of the formula (5) can be recovered in the same manner as above, and can be reused. However, since the halogen atom of the compound of the formula (5) is highly active, the formed compound of the formula (3) is condensed further with the excess of the compound of the formula (5) to produce as a by-product a compound of the formula,

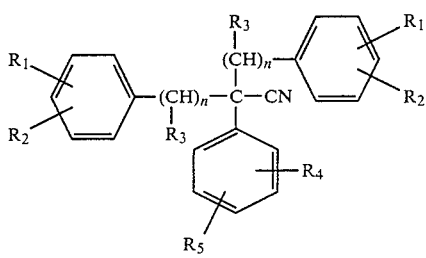

wherein $R_1$, $R_2$, $R_3$, $R_4$, $R_5$ and n have the same meanings as above, lowering of the yield of the desired compound of the formula (3). Therefore, it is preferable to use the compound of the formula (5) in an equimolar amount or less. However, the by-produced compound of the above formula is not subject to hydrolysis, and has no influence on the next reaction step.

The condensation is carried out in the presence or absence of a solvent. The solvents used for the reaction are illustrated, for example, by water, alcohols such as methanol, ethanol, isopropylalcohol, hexanol and butanols, benzene, toluene, xylene, chlorobenzenes, hexane, heptane, methyl cellosolve, dioxane, tetrahydrofuran, dimethylformamide, ether, dimethylsulfoxide etc. They can be used alone or in mixture. Further, the compound of the formula (4) can be used as solvent as mentioned above. When the compounds of the formulas (3), (4) and (5) are solid at room temperature, it is more preferable from the point of practice to use a solvent capable of dissolving these compounds. Furthermore, a compound of the following formula,

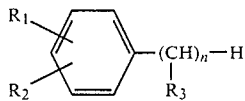

wherein $R_1$, $R_2$, $R_3$ and n have the same meanings as above, can be used as the solvent.

While, the compound of the formula (5) can be produced by halogenation of the compound of the above formula, and therefore in the preparation of the compound of the formula (5), if the halogenation is controlled to decrease the conversion and to increase the selectivity of the monohalide [the compound of the formula (5)], the resulting reaction mixture can be used as it is without separation of the compound of the formula (5).

As the base to be used, alkali metals, alkali metal hydroxides, alkali metal carbonates, alkali metal alkoxides, alkali metal hydrides etc. are illustrated. The amounts thereof are 1 to 8 mols, preferably 1 to 4 mols, per mol of the raw material, the compound of the formula (4).

In this reaction, the base is consumed in an equimolar amount to the compound of the formula (5), and an excess base, if any, may be separated or the reaction mixture may be used for the next step as it is without separating the excess base.

An organic quaternary ammonium salt or tertiary amine is added in a catalytic amount to the reaction system to relatively accelerate the reaction velocity and to increase the conversion, whereby the compound of the formula (3) is obtained in a high yield. Therefore it is preferable to use these compounds as a catalyst. Examples of the organic quaternary ammonium salt or tertiary amine include tetraethylammonium-chloride, -bromide or -hydroxide, tetra-n-butylaminomin-chloride, -bromide or -hydroxide, triethylbenzylammonium-chloride, -bromide or -hydroxide, trimethylamine, triethylamine, tributylamine, tripropylamine and the like.

These compounds can be used alone or in mixture. The amount of these catalysts is in a range of 1/200 to 1/5 mol per mol of the compound of the formula (4), but in general, the amount is almost 1/100 mol.

The catalyst can be recovered after completion of the reaction and reused.

The reaction temperature can optionally be determined within a range of $-20°$ to $200°$ C., but preferably it is within a range of $0°$ to $100°$ C.

As to the reaction pressure, there is no limitation, and thus the reaction may be carried out either under atmospheric pressure or under increased pressure. The reaction may be carried out in either batch system or continuous system.

The resulting reaction mixture can be subjected to after-treatments such as separation, concentration, distillation, crystallization, etc., whereby the compound of the formula (3) can be obtained in a good yield. However, it is not always necessary to isolate the compound of the formula (3) from the reaction mixture, and the reaction mixture can be used in the next step (2) as it is, to obtain the compound of the formula (2).

In the hydrolysis of the compound of the formula (3) to obtain the compound of the formula (2) (step 2), any hydrolysis method such as hydrolysis using a base, acid or metal catalyst etc. can be used and any one of them can arbitrarily be selected for use.

As the base to be used as a catalyst for example, alkali metal hydroxides, alkali metal carbonates, alkali metal alkoxides, alkaline earth metal hydroxides, etc. are illustrated, and as the acid, sulfuric acid, hydrochloric acid, phosphoric acid, polyphosphoric acid, acetic acid, nitric acid, hydrobromic acid, formic acid, etc. are illustrated, and as the metal catalyst, copper sulfate, copper oxide, copper chloride, copper hydride, copper acetate, copper-vanadium alloy, copper magnesium chrome silicate, chromium oxide, manganese dioxide, palladium chloride, rhodium chloride, ruthenium chloride, etc. are illustrated. The reaction is carried out in the absence or presence of a solvent, the solvent being the same as in the step (1).

The presence of the same organic quaternary ammonium salts and/or tertiary amines as described hereinafter in the production of the amide derivative of the formula (I), in the above reaction system is favorable to allow the reaction to proceed at relatively low temperature and to increase the reaction velocity. The amount thereof can be determined in such a manner as described in the production of the amide derivative of the formula (I).

The reaction can be ordinarily carried out at a temperature of 0° to 300° C., preferably at 20° to 250° C.

There is no limitation on reaction pressure and the reaction may be carried out under atmospheric pressure or under increased pressure.

Further, the reaction may be conducted in a vapor phase or in a liquid phase, and the process may be carried out in a batch system or continuous system.

In some cases in this reaction, a compound of the formula,

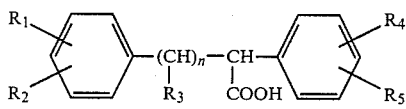

wherein $R_1$, $R_2$, $R_3$, $R_4$, $R_5$ and n have the same meanings as above, may be by-produced due to further hydrolysis of the desired compound (2), decreasing the yield of the desired compound. However, in such case, it is also possible to decrease the by-production of said undesired compound by controlling the conversion, recovering and reusing the unreacted compound of the formula (3). In addition, the existence of hydrogen peroxide or dimethylsulfoxide in the reaction system decreases the by-production of the undesired compound. In this case, hydrogen peroxide is used in an amount of more than 1 mol, preferably 2 to 10 mols, per mol of the compound of the formula (3). The reaction temperature in this case is preferable in a range of 20° to 80° C. Although the reaction time varies depending upon the amount of hydrogen peroxide used, ordinarily the reaction is completed within a range of 30 minutes to 10 hours. In the case of using hydrogen peroxide, the reaction may be advanced in a solvent of water alone, but the simultaneous use of alcohols such as methanol, ethanol, isopropanol etc. is recommended for the reason that the simultaneous use of alcohols makes the reaction system homogeneous and increases the reaction velocity. In the case of simultaneous use of the base and dimethylsulfoxide, dimethylsulfoxide is arbitrarily used in an amount more than 1 mol per mol of the compound of the formula (3). It is preferred to control the amount of dimethylsulfoxide to 2 to 10 mols from the viewpoint of the solubility of the compound of the formula (3) in dimethylsulfoxide and from the economical point of view because it is somewhat difficult to recover dimethylsulfoxide from the aqueous solution thereof due to its good solubility in water. The reaction is conducted at a temperature of 60° to 150° C., preferably 80° to 130° C., and is ordinarily completed within ten hours.

Of the hydrolysis methods described above, the hydrolysis method as described in the production of the amide derivative of the formula (I) is most effectively applied for this step (2), that is, the hydrolysis of the compound of the formula (3) is carried out using as a catalyst the organic quaternary ammonium salt and/or tertiary amine in the presence of the base and hydrogen peroxide.

The resulting hydrolysis reaction mixture is subjected to after-treatments such as separation, concentration, distillation, crystallization, etc. to obtain the compound of the formula (2) in a good yield. However, it is not always necessary to separate the compound of the formula (2) from the reaction mixture for the subsequent decomposition reaction to obtain the amine derivative of the formula (1) and the reaction mixture may be brought to the next step as it is.

Finally, the step (3) to obtain the compound of the formula (1) by way of alkali decomposition of the compound of the formula (2) will be discussed in detail in the following.

The step (3) is the so-called Hofmann reaction and the compound of the formula (1) is obtained by allowing the compound of the formula (2) to react with a halogen, alkali metal hypohalite or alkaline earth metal hypohalite in the presence of a base.

In this step, the presence of an organic quaternary ammonium salt or teartiary amine accelerates the reaction to allow the reaction to proceed at a relatively low temperature, and to improve the reaction velocity.

The base to be used includes alkali metal hydroxides, alkali metal carbonates, alkali metal alkoxides, alkaline earth metal hydroxides and the like.

The base is arbitrarily used in an amount of more than 2 mols, preferably 2 to 10 mols, per mol of compound of the formula (2).

As the halogen, chlorine, bromine, fluorine etc. are illustrated. Such halogen is used arbitrarily in an amount of more than 1 mol, preferably 1 to 5 mols, per mol of the compound of the formula (2). In this case, the base is preferably used in an amount of more than 4 mols per mol of the compound of the formula (2).

As the alkali metal hypohalite or alkaline earth metal hypohalite, sodium hypochlorite, potassium hypochlorite, sodium hypobromite, potassium hypobromite, calcium hypochlorite, calcium hypobromite, etc. are illustrated.

Such alkali metal hypohalite or alkaline earth metal hypohalite is used arbitrarily in an amount of more than 1 mol, preferably 1 to 5 mol, per mol of the compound of the formula (2).

As the organic quaternary ammonium salt or tertiary amine, those used in the step (1) for obtaining the compound of the formula (3) from the compound of the formula (4) and the compound of the formula (5) are also used, and the amount thereof is also determined in such a manner as described in the step (1).

As the solvent, the same one as in the step (1) is also usable. In the case of using alcohols such as methanol, ethanol, etc. as a solvent, the compound of the formula (2) is sometimes converted into the compound of the formula (1) through a carbamate derivative of the formula,

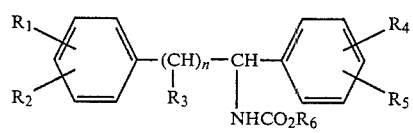

wherein $R_1$, $R_2$, $R_3$, $R_4$, $R_5$ and n have the same meanings as above, and $R_6$ signifies an alkyl group such as methyl, ethyl, etc. However, the invention is not concerned with the formation of the carbamate.

The reaction temperature is arbitrarily determined within the range of −20° to 150° C., preferably −10° to 100° C.

The reaction pressure has no limitation and atmospheric pressure as well as increased pressure are arbitrarily used.

The reaction can be carried out in batch system or in continuous system. The reaction is ordinarily completed within 20 hours.

From the reaction mixture thus obtained, the compound of the formula (1) can be obtained in a good yield using such procedures as separation, concentration, distillation, crystallization, etc.

As the compound of the formula (1), the followings are illustrated:

For example, there are mentioned α-(o-, m- or p-chlorophenyl)-β-phenylethylamine,
α-(o-, m- or p-bromophenyl)-β-phenylethlamine,
α-(o-, m- or p-fluorophenyl)-β-phenylethylamine,
α-(o-, m- or p-methoxyphenyl)-β-phenylethylamine,
α-(o-, m- or p-ethoxyphenyl)-β-phenylethylamine,
α-(o-, m- or p-phenoxyphenyl)-β-phenylethylamine,
α-(o-, m- or p-phenylthiophenyl)-β-(o-, m- or p-chlorophenyl)-ethylamine,
α-(o-, m- or p-methylthiophenyl)-β-(o-, m- or p-bromophenyl)-ethylamine,
α-(o-, m- or p-dimethylaminophenyl)-β-(o-, m- or p-fluorophenyl)-ethylamine,
α-(o-, m- or p-methylsulfonylphenyl)-β-(o-, m- or p-methoxyphenyl)-ethylamine,
α-(o-, m- or p-isopropenylphenyl)-β-(o-, m- or p-ethoxyphenyl)-ethylamine,
α-(o-, m- or p-tolyl)-β-(o-, m- or p-phenoxyphenyl)-ethylamine,
α-(o-, m- or p-ethylphenyl)-β-(o-, m- or p-methylthiophenyl)-ethylamine,
α-(o-, m- or p-propylphenyl)-β-(o-, m- or p-phenylthiophenyl)-ethylamine,
α-(o-, m- or p-butylphenyl)-β-(o-, m- or p-dimethylaminophenyl)-ethylamine,
α-(o-, m- or p-isopropylphenyl)-β-(o-, m- or p-methylsulfonylphenyl)-ethylamine,
α-(o-, m- or p-isobutylphenyl)-β-(o-, m- or p-isopropenylphenyl)-ethylamine,
α-(o-, m- or p-trichloromethylphenyl)-β-(o-, m- or p-isobutylphenyl)-ethylamine,
α-(o-, m- or p-trifluoromethylphenyl)-β-(o-, m- or p-isopropylphenyl)-ethylamine,
α-(o-, m- or p-hydroxymethylphenyl)-β-(o-, m- or p-butylphenyl)-ethylamine,
α-phenyl-β-(o-, m- or p-propylphenyl)-ethylamine,
α-phenyl-β-(o-, m- or p-ethylphenyl)-ethylamine,
α-phenyl-β-(o-, m- or p-tolyl)-ethylamine,
α-phenyl-β-(o-, m- or p-trichloromethylphenyl)-ethylamine,
α-phenyl-β-(o-, m- or p-trifluoromethylphenyl)-ethylamine,
α-(3,4-dimethoxyphenyl)-β-phenylethylamine,
α-(3,4-dichlorophenyl)-β-phenylethylamine,
α-(3,5-dichlorophenyl)-β-phenylethylamine,
α-(2,4-dichlorophenyl)-β-phenylethylamine,
α-(3,4-xylyl)-β-phenylethylamine,
α-(2,5-xylyl)-β-(3,4-dimethoxyphenyl)-ethylamine,
α-(2,4-xylyl)-β-(3,4-dichlorophenyl)-ethylamine,
α-(3,4-methyleneoxyphenyl)-β-(3,5-dichlorophenyl)-ethylamine,
α-(3,4-dibromophenyl)-β-(2,4-dichlorophenyl)-ethylamine,
α-(2,5-dibromophenyl)-β-(3,4-xylyl)-ethylamine,
α-(2,4-dibromophenyl)-β-(2,5-xylyl)-ethylamine,
α-(3,4-difluorophenyl)-β-(2,4-xylyl)-ethylamine,
α-(2,5-difluorophenyl)-β-(3,4-methyleneoxyphenyl)-ethylamine,
α-phenyl-β-(3,4-dibromophenyl)-ethylamine,
α-phenyl-β-(2,5-dibromophenyl)-ethylamine,
α-phenyl-β-(2,4-dibromophenyl)-ethylamine,
α-phenyl-β-(3,4-difluorophenyl)-ethylamine,
α-phenyl-β-(2,5-difluorophenyl)-ethylamine,
α-phenyl-β-methyl-β-(o-, m- or p-tolyl)-ethylamine,
α-phenyl-β-methoxy-β-(o-, m- or p-tolyl)-ethylamine,
α-phenyl-β-methoxy-β-(o-, m- or p-methylsulfonylphenyl)-ethylamine,
1-(o-, m- or p-methylphenyl)-3-phenylpropylamine,
1-(2,4-dichlorophenyl)-3-phenylpropylamine,
1-(3,4-methoxyphenyl)-4-phenylbutylamine, and the like.

If desired, the compounds of the formula (1) can be optionally resolved by using a proper optically resolving agent. Particularly, as a result of extensive studies to find a process for optically resolving dl-α-(o-, m- or p-chlorophenyl)-β-phenylethylamine, it has been found that the particular amine, dl-α-(o-, m- or p-chlorophenyl)-β-phenylethylamine can be effectively optically resolved only by using optically active tartaric acid, whereas optically active malic acid, aspartic acid and other optically resolving agents are incapable of optically resolving the particular amine or only give the desired optically active amine with poor optical purity.

The optically active α-(o-, m- or p-chlorophenyl)-β-phenylethylamine is novel and useful, particularly as an optically resolving agent for medicines, agricultural chemicals or the like.

In carrying out the optical resolution using optically active tartaric acid, the particular amine is contacted with optically active tartaric acid (about 0.5 to about 1 mole, preferably 1 mole, per mole of the amine) in a solvent to form diastereoisomeric salts.

The solvents to be used includes acetone, methanol, ethanol, isopropanol or an aqueous mixture thereof, ethyl acetate, toluene, chloroform or a mixture thereof.

The formation of diastereoisomeric salts is carried out at a temperature of −20° C. to boiling point of the solvent used, preferably at a temperature higher than that at which the diastereoisomeric salts are crystallized.

After the formation of diastereoisomeric salts, the mixture is gradually cooled to crystallize one of the diastereoisomeric salts. The crystals are separated by filtration and dried, and then subjected to decomposition using an alkali aqueous solution.

The alkali used includes sodium hydroxide, potassium hydroxide, sodium carbonate, potassium carbonate and the like.

The amount of the alkali to be used is arbitrarily selected in the range of not less than 1 mole per mole of the salt, but is practically sufficient in an amount of about 1 to 1.2 moles.

After extraction thereof using an organic solvent, e.g. toluene, chloroform, ether, benzene and the like, the extract is washed with water. Evaporation of the solvent gives optically active α-(o-, m- or p-chlorophenyl)-β-phenylethylamine.

In this manner, the l-isomer of the particular amine is obtained using L-(+)-tartaric acid, and the d-isomer using D-(−)-tartaric acid.

On the other hand, the relatively more soluble diastereoisomeric salt can be isolated from the filtrate by a conventional method, for example, by repeating a procedure wherein the filtrate is concentrated to deposit crystals, which are then separated by filtration.

The invention is illustrated by way of examples in the following with an intention only for illustration and without any intention to add any limitations to the invention. In the Examples, percents are by weight.

PRODUCTION OF AMINE DERIVATIVES OF THE FORMULA (1)

EXAMPLE 1

117.2 Grams of benzylnitrile [(4)-1], 84.4 g of p-methylbenzylchloride [(5)-1], 640 g of a 25% aqueous sodium hydroxide solution and 3.22 g of tetra-n-butylammonium bromide were stirred at 60° C. for 2 hours in 117.2 g of toluene. After the reaction was completed, the aqueous layer was separated and the organic layer was distilled to recover toluene and 49.2 g of unreacted benzylnitrile. The concentrated residue was further distilled to obtain 119.5 g of α-phenyl-β-(p-tolyl)-propionitrile [(3)-1].

Yield was 95% based on the reacted nitrile [(4)-1].

119.5 Grams of the obtained p-phenyl-β-(p-tolyl)-propionitrile [(3)-1], 21.6 g of a 25% aqueous sodium hydroxide solution, 209.9 g of a 35% aqueous hydrogen peroxide solution and 1.74 g of tetra-n-butylammonium bromide were reacted at 50° C. for 3 hours in 358.5 g of methanol.

After the reaction was completed, the precipitate was formed by distilling off methanol from the reaction mixture and was filtered out and washed with water to obtain 126.6 g of α-phenyl-β-(p-tolyl)-propionamide [(2)-1] (m.p.: 150°–151° C.) in a yield of 98%.

Then, to 126.6 g of the obtained amide [(2)-1] and 211.6 g of sodium hydroxide, was added 379.8 g of methanol as a solvent. 109.9 Grams of bromine was added dropwise to the reaction mixture at 0° C. with stirring during 2 hours. The reaction mixture was kept at 60° C. for 2 hours, and further 1.70 g of tetra-n-butylammonium bromide was added thereto to react under reflux for 10 hours. After the reaction was completed, the reaction mixture was allowed to distill off methanol and then extracted with toluene. After separation, the organic layer was allowed to distill off toluene to obtain 109.6 g of α-phenyl-β-(p-tolyl)-ethylamine [(1)-1] (b.p.: 131.0° C./1 mmHg) in a yield of 98%.

EXAMPLE 1-1

221.3 Grams of the nitrile [(3)-1] obtained in Example 1 and 13.2 g of sodium hydroxide were stirred at 110° C. for 4 hours in 398.3 g of dimethylsulfoxide.

After the reaction was completed, the precipitate was formed by distilling off dimethylsulfoxide and adding 663.9 g of water to the residue, and then was filtered and washed with water to obtain 232.1 g of α-phenyl-β-(p-tolyl)-propionamide [(2)-1] in a yield of 97%.

In the same manner as in Example 1, the resulting amide [(2)-1] was subjected to alkali-decomposition to obtain the amine [(1)-1] in a yield of 98%.

EXAMPLE 1-2

221.3 Grams of the nitrile [(3)-1] obtained in Example 1 and 224.4 g of potassium hydroxide were stirred under reflux for 3 hours in 1106.5 g of t-butanol.

After the reaction was completed, the precipitate was formed by distilling off t-butanol and adding 663.9 g of water to the residue and then was filtered and washed with water to obtain 234.5 g of the amide [(2)-1] in a yield of 98%.

In the same manner as in Example 1, the resulting amide [(2)-1] was subjected to alkali-decomposition to obtain the amine [(1)-1] in a yield of 98%.

EXAMPLE 1-3

221.3 Grams of the nitrile [(3)-1] obtained in Example 1 was reacted with 442.6 g of 65% sulfuric acid at 140° to 145° C. for 1 hour.

After the reaction was completed, the reaction mixture was cooled, and was neutralized with aqueous 45% sodium hydroxide solution. The formed precipitate was filtered and washed with water to obtain 203.4 g of α-phenyl-β-(p-tolyl)-propionamide [(2)-1] in a yield of 85%.

In the same manner as in Example 1, the resulting amide [(2)-1] was subjected to alkali-decomposition to obtain the amine [(1)-1] in a yield of 98%.

EXAMPLE 1-4

221.3 Grams of α-phenyl-β-(p-tolyl)-propionitrile [(3)-1] obtained in Example 1 was prewarmed at 90° C., and passed into the bottom of a reacting tube having jacket and filled with manganese dioxide to react. The reaction tube was kept at 90° C. and mean residence time was 1 hour.

By chromatographic analysis of the reaction mixture flowed out of the top of the reaction tube, α-phenyl-β-(p-tolyl)-propionamide [(2)-1] was obtained at a selectivity of 95% and a nitrile conversion of 30%.

In the same manner as in Example 1, the resulting amide [(2)-1] was subjected to alkali-decomposition to obtain the amine [(1)-1] in a yield of 98%.

EXAMPLE 2

To 239.3 g of α-phenyl-β-(p-tolyl)-propionamide (2)-1 obtained in the same manner as in Example 1 and 162.1 g of sodium methoxide was added 717.9 g of methanol as a solvent. At 0° C. under stirring, 207.8 g of bromine was added dropwise during 2 hours to the reaction mixture. The reaction mixture was kept at 60° C. for 2 hours and then 561 g of potassium hydroxide, 393 g of water and 717.9 g of methanol were added to the reaction mixture and the reaction was continued under reflux for 5 hours. After completion of the reaction, the reaction mixture was allowed to distill off methanol and then extracted with toluene. After separation, the organic layer was allowed to distill off toluene to obtain 207.1 g of α-phenyl-β-(p-tolyl)-ethylamine in a yield of 98%.

EXAMPLE 3

145.3 Grams of 2,4-dimethylbenzylnitrile [(4)-2], 118.5 g of 3,4-dichlorobenzylchloride [(5)-2], 897.6 g of a 25% aqueous potassium hydroxide solution and 26.0 g of a 10% aqueous tetra-n-butylammonium hydroxide solution were stirred at 60° C. for 2 hours in 145.3 g of benzene. After completion of the reaction, the water layer was separated. The organic layer was distilled to recover benzene and 62.5 g of the unreacted 2,4-dimethylbenzylnitrile. By the chromatographic analysis of the concentrated residue, α-2,4-xylyl-β-(3,4-dichlorophenyl)-propionitirle [(3)-2] was found to have been obtained in a selectivity of 94% for the reacted nitrile [(4)-2].

Then, the concentrated residue obtained in the above, 14.0 g of sodium carbonate, 206.0 g of a 35% aqueous hydrogen peroxide solution and 1.21 g of triethylbenzylammonium chloride were reacted at 50° C. for 4 hours in 470 g of isopropanol and 42 g of water. After completion of the reaction, the reaction mixture was analyzed by gas-chromatography to show the selectivity of α-2,4-xylyl-β-(3,4-dichlrophenyl)-propionamide [(2)-2] of 96% for [(3)-2] in the concentrated residue.

Then, 106 g of sodium hydroxide was added to the reaction mixture obtained in the above, and 592 g of a 10% aqueous NaOCl solution was added dropwise thereto during 2 hours. Then, the reaction mixture was heated at 60° C. for 4 hours. After completion of the reaction, the reaction mixture was allowed to distill off isopropanol and then extracted with toluene. After separation, by gas-chromatographic analysis, the organic layer was formed to obtain α-2,4-xylyl-β-(3,4-dichlorophenyl)-ethylamine in a selectivity of 90% for the amide [(2)-2] in the reaction mixture.

EXAMPLE 4

133.2 Grams of m-hydroxybenzylnitrile [(4)-3], 75.9 g of benzyl chloride [(5)-3], 640 g of a 25% aqueous sodium hydroxide solution and 2.62 g of triethylamine were stirred at 60° C. for 4 hours in 133.2 g of toluene. After completion of the reaction, the water layer was separated. The organic layer was distilled to recover toluene and 58.6 g of the unreacted m-hydroxybenzylnitrile. The gas-chromatographyic analysis of the concentrated residue showed that α-(m-hydroxyphenyl)-β-phenylpropionitrile [(3)-3] was obtained in a selectivity of 93% for the reacted raw nitrile [(4)-3].

Subsequently, the concentrated residue obtained in the above, 20.8 g of a 25% aqueous sodium hydroxide solution, 202.1 g of a 35% aqueous hydrogen peroxide solution and 1.78 g of tributylamine were reacted at 50° C. for 3 hours in 333 g of ethanol. After completion of the reaction, the gas-chromatographic analysis of the reaction mixture showed that α-(m-hydroxyphenyl)-β-phenylpropionamide [(2)-3] was obtained in a selectivity of 97% for the nitrile [(3)-3] in the concentrated residue.

Following this, to the reaction mixture obtained in the above was added 145.6 g of sodium hydroxide. 108.0 Grams of bromine were added dropwise at 0° C. with stirring to the mixture during 2 hours and the reaction mixture was kept at 60° C. for 2 hours. The reaction mixture was further reacted under reflux for 10 hours.

After completion of the reaction, ethanol was distilled off. The concentrated residue was extracted with toluene and separated. The obtained organic layer was gas-chromatographically analyzed and the results showed that α-(m-hydroxyphenyl)-β-phenylethylamine was obtained in a selectivity of 90% for the amide [(2)-3] in the reaction mixture.

EXAMPLES 5–24

The above Examples were repeated, provided that there were used starting materials as shown in Table 1 with the results also as shown in Table 1.

TABLE 1

| Example No. | Raw Material Compound having the formula (4) | Raw Material Compound having the formula (5) | 1st Step Reaction Condition | 1st Step Yield or Selectivity** | 2nd Step Reaction condition | 2nd Step Yield or Selectivity** | 3rd Step Reaction Condition | 3rd Step Yield or Selectivity** |
|---|---|---|---|---|---|---|---|---|
| 5 | p-methylbenzylnitrile | p-methylbenzylchloride | Same as Example 1 | 95% | Same as Example 1 | 98% | Same as Example 1 | 98% |
| 6 | p-chlorobenzylnitrile | " | Same as Example 1 | 95% | Same as Example 1-1 | 97% | Same as Example 1 | 98% |
| 7 | m-bromobenzylnitrile | " | Same as Example 1 | 97% | Same as Example 1-2 | 98% | Same as Example 1 | 98% |
| 8 | 2,5-diethylbenzylnitrile | " | Same as Example 1 | 95% | Same as Example 1-3 | 84% | Same as Example 1 | 98% |
| 9 | o-methoxybenzylnitrile | " | Same as Example 1 | 96% | Same as Example 1-4 | 94%* | Same as Example 1 | 98% |
| 10 | p-dimethylaminobenzylnitrile | " | Same as Example 1 | 95% | Same as Example 1 | 98% | Same as Example 2 | 98% |
| 11 | 2,4-dimethylbenzylnitrile | p-methyl-α-ethyoxybenzylchloride | Same as Example 3 | 94% | Same as Example 3 | 96% | Same as Example 3 | 91% |
| 12 | m-hydroxybenzylnitrile | p-propylbenzylchloride | Same as Example 4 | 93% | Same as Example 4 | 96% | Same as Example 4 | 91% |
| 13 | o-ethylbenzylnitrile | p-dimethylaminobenzylchloride | Same as Example 3 | 94% | Same as Example 3 | 97% | Same as Example 3 | 88% |
| 14 | benzylnitrile | benzylchloride | Same as Example 3 | 96% | Same as Example 3 | 96% | Same as Example 3 | 89% |
| 15 | 2,5-dibromobenzylnitrile | 3,4-dimethoxybenzylchloride | Same as Example 3 | 94% | Same as Example 3 | 95% | Same as Example 3 | 90% |
| 16 | p-propylbenzylnitrile | p-methylthiobenzylchloride | Same as Example 3 | 95% | Same as Example 3 | 95% | Same as Example 3 | 89% |
| 17 | 2,5-difluorobenzylnitrile | m-phenylthiobenzylchloride | Same as Example 3 | 93% | Same as Example 3 | 97% | Same as Example 3 | 91% |
| 18 | o-isopropenylbenzylnitrile | p-methyl-α-methoxybenzylchloride | Same as Example 3 | 94% | Same as Example 3 | 96% | Same as Example 3 | 90% |
| 19 | o-trichloromethylbenzylnitrile | p-hydroxybenzylchloride | Same as Example 4 | 93% | Same as Example 4 | 97% | Same as Example 4 | 88% |
| 20 | m-methylbenzylnitrile | o-ethylbenzylchloride | Same as Example 4 | 93% | Same as Eample 4 | 97% | Same as Example 4 | 89% |
| 21 | benzylnitrile | m-chlorobenzylchloride | Same as Example 4 | 94% | Same as Example 4 | 96% | Same as Example 4 | 88% |

TABLE 1-continued

| Example No. | Raw Material | | 1st Step | | 2nd Step | | 3rd Step | |
|---|---|---|---|---|---|---|---|---|
| | Compound having the formula (4) | Compound having the formula (5) | Reaction Condition | Yield or Selectivity** | Reaction condition | Yield or Selectivity** | Reaction Condition | Yield or Selectivity** |
| 22 | " | p-fluorobenzylchloride | Same as Example 4 | 95% | Same as Example 4 | 95% | Same as Example 4 | 90% |
| 23 | " | phenethylchloride | Same as Example 4 | 93% | Same as Example 4 | 97% | Same as Example 4 | 91% |
| 24 | " | phenylpropylchloride | Same as Example 4 | 94% | Same as Example 4 | 98% | Same as Example 4 | 92% |

*Selectivity at a conversion ratio 30% of the raw nitrile.
**In all of the Examples same as Examples 3 and 4, "Selectivity" is given.

EXAMPLE 25

Using p-chlorobenzylnitrile and benzyl chloride, the first, second and third steps were carried out in the same manner as in Example 1 to obtain α-(p-chlorophenyl)-β-phenylethylamine (m.p. 35°–36° C.) in a yield of 95, 98 and 97% in the first, second and third steps, respectively.

A mixture of the thus obtained α-(p-chlorophenyl)-β-phenylethylamine (231.7 g), ethanol (1000 g) and L-(+)-tartaric acid (150.1 g) was stirred under reflux at 80° C. for 1 hour. The mixture was gradually cooled and maintained at 25° C. for 2 hours. The produced crystals were separated by filtration and dried, and then subjected to decomposition with the aid of a 10% aqueous sodium hydroxide solution (120 g). After extraction thereof using toluene (100 g), the extract was washed twice with water (50 g). Evaporation of the toluene gave 57.5 g of l-α-(p-chlorophenyl)-β-phenylethylamine ($[α]_D^{25}= -100.2°$ (c=1, methanol), m.p. 65.0°–66.0° C.) in a resolution yield of 50.0%.

Elementary analysis:

| | Found | Calculated as $C_{14}H_{14}NCl$ |
|---|---|---|
| C (%) | 72.62 | 72.57 |
| H (%) | 6.21 | 6.09 |
| N (%) | 5.93 | 6.04 |
| Cl (%) | 15.21 | 15.30 |

The filtrate freed from the crystals was concentrated to produce crystals, which were separated by filtration. This procedure was repeated and thereafter the solvent was distilled off completely from the resulting filtrate. The residue was subjected to alkali-decomposition, extraction and evaporation in the same manner as above, whereby there was obtained d-α-(p-chlorophenyl)-β-phenylethylamine having the same physical properties as those of the above l-isomer excepting specific rotation $[α]_D^{25}= +100.2°$.

EXAMPLE 26

A mixture of α-(o-chlorophenyl)-β-phenylethylamine (231.7 g), methanol (1350 g), water (150 g) and L-(+)-tartaric acid (150.1 g) was refluxed at 70° C. for 1 hour and then gradually cooled to 30° C. at which the mixture was kept for 2 hours. The produced crystals were separated by filtration, dried and then subjected to decomposition using a 10% aqueous sodium hydroxide solution (100 g). After extraction thereof using benzene (100 g), the extract was washed twice with water (50 g). Evaporation of the benzene gave 52.4 g of l-α-(o-chlorophenyl)-β-phenylethylamine ($[α]_D^{25}= -34.0°$ (neat), b.p. 142° to 145° C./2 mmHg) in a resolution yield of 45.2%.

Elementary analysis:

| | Found | Calculated as $C_{14}H_{14}NCl$ |
|---|---|---|
| C (%) | 72.64 | 72.57 |
| H (%) | 6.19 | 6.09 |
| N (%) | 5.95 | 6.04 |
| Cl (%) | 15.20 | 15.30 |

The filtrate was treated in the same manner as in Example 25 to obtain d-α-(o-chlorophenyl)-β-phenylethylamine having specific rotation $[α]_D^{25}= +34.0°$ (neat).

EXAMPLE 27

A mixture of α-(m-chlorophenyl)-β-phenylethylamine (231.7 g), ethanol (1800 g), water (200 g) and L-(+)-tartaric acid (150.1 g) was refluxed at 80° C. for 1 hour and then gradually cooled to 25° C. at which the mixture was kept for 2 hours. The produced crystals were separated by filtration, dried and then subjected to alkali-decomposition using a 10% aqueous sodium hydroxide solution (100 g). After extraction thereof using toluene (100 g), the extract was washed twice with water (50 g). Evaporation of the toluene gave 55.6 g of l-α-(m-chlorophenyl)-β-phenylethylamine ($[α]_D^{25}= -27.2°$ (neat), b.p. 147° to 150° C./2 mmHg) in a resolution yield of 48.0%.

Elementary analysis:

| | Found | Calculated as $C_{14}H_{14}NCl$ |
|---|---|---|
| C (%) | 72.59 | 72.57 |
| H (%) | 6.23 | 6.09 |
| N (%) | 5.90 | 6.04 |
| Cl (%) | 15.19 | 15.30 |

The filtrate was treated in the same manner as in Example 25 to obtain d-α-(m-chlorophenyl)-β-phenylethylamine having specific rotation $[α]_D^{25}= +27.2°$ (neat).

EXAMPLE 28

A mixture of α-(p-chlorophenyl)-β-phenylethylamine (231.7 g), ethanol (1000 g) and D-(−)-tartaric acid (150.1 g) was refluxed at 80° C. for 1 hour, and then gradually cooled to 25° C. at which the mixture was kept for 2 hours. The produced crystals were separated by filtration, dried and then subjected to alkali-decomposition using a 10% aqueous sodium hydroxide solution (120 g). After extraction thereof using toluene (100 g), the extract was washed twice with water (50 g).

Evaporation of the toluene gave 57.3 g of d-α-(p-chlorophenyl)-β-phenylethylamine ([α]$_D^{25}$=+100.2° (C=1, methanol), m.p. 65.0° to 66.0° C.) in a resolution yield of 49.5%.

Elementary analysis:

|  | Found | Calculated as C$_{14}$H$_{14}$NCl |
|---|---|---|
| C (%) | 72.65 | 72.57 |
| H (%) | 6.15 | 6.09 |
| N (%) | 5.96 | 6.04 |
| Cl (%) | 15.36 | 15.30 |

PRODUCTION OF AMIDE DERIVATIVES OF THE FORMULA (I)

EXAMPLES 29 TO 31

221.3 Grams of 2-phenyl-3-(p-tolyl)-propionitrile (II-1), 40 g of a 25% aqueous sodium hydroxide solution, 291.5 g of a 35% aqueous hydrogen peroxide solution and 3.22 g of tetra-n-butylammoniumbromide were mixed at 50° C. for 4 hours in 663.9 g of methanol. After the reaction was completed, methanol was distilled off. The formed precipitates were filtered out, and washed with water to obtain 234.5 g of 2-phenyl-3-(p-tolyl)-propionamide (m.p.: 150°–151° C.) (I-I) in a yield of 98%.

Using 2-phenylpropionitrile and acrylonitrile as raw materials, the reactions were carried out as in the above to obtain the amide compounds. The results were obtained as shown in the following Table 2.

Further, in comparative examples, reactions using no catalyst (organic quaternary ammonium salt) were carried out and the amides were prepared. The results are also shown in Table 2.

TABLE 2

|  | Raw Material | Catalyst | Reaction Hour | Yield |
|---|---|---|---|---|
| Example 29 | 2-phenyl-3-(p-tolyl)-propionitrile | tetra-n-butylammonium bromide | 4 | 98% |
| Example 30 | 2-phenyl-propionitrile | tetra-n-butylammonium chloride | 4 | 97% |
| Example 31 | acrylonitrile | triethyl-benzyl-ammonium chloride | 4 | 98% |
| Comparative Example 1 | 2-phenyl-3-(p-tolyl)-propionitrile | none | 15 | 90% |
| Comparative Example 2 | 2-phenyl-propionitrile | " | 10 | 89% |
| Comparative Example 3 | acrylonitrile | " | 7 | 91% |

In comparison of Example 29 with Comparative Example 1, the relations between the reaction time and yield are shown in the attached Figure. In the Figure, (A) shows the result of Example 29 and (B) that of Comparative Example 1.

EXAMPLE 32

221.3 Grams of 2-phenyl-3-(p-tolyl)-propionitrile (II-1), 40 g of a 25% aqueous sodium hydroxide solution, 291.5 g of a 35% aqueous hydrogen peroxide solution and 2.78 g of tetra-n-butylammonium chloride were mixed at 50° C. for 4 hours in 663.9 g of methanol. After the reaction was completed, methanol was distilled off and the formed precipitate was filtered out and washed with water to obtain 234.5 g of 2-phenyl-3-(p-tolyl)-propionamide (m.p.: 150°–151° C.) (I-1) in a yield of 98%.

EXAMPLE 33

117.2 Grams of phenylacetonitrile (II-2), 56.1 g of a 25% aqueous potassium hydroxide solution, 291.5 g of a 35% aqueous hydrogen peroxide solution and 1.78 g of triethylbenzylammonium chloride were mixed at 50° C. for 4 hours in 351.6 g of isopropanol. After completion of the reaction, isopropanol was distilled off and the formed precipitate was filtered out and washed with water to obtain 128.5 g of phenylacetamide (m.p.: 155° C.) (I-2) in a yield of 95%.

EXAMPLE 34

41.1 Grams of acetonitrile (II-3), 40 g of a 25% aqueous sodium hydroxide solution, 291.5 g of a 35% aqueous hydrogen peroxide solution and 1.01 g of triethylamine were mixed at 50° C. for 4 hours. After the reaction was completed, the formed precipitate was filtered out, and washed with water to obtain 56.1 g of acetamide (m.p.: 81° C.) (I-3) in a yield of 95%.

EXAMPLE 35

103.1 Grams of benzonitrile (II-4), 9.51 g of sodium methoxide, 291.5 g of a 35% aqueous hydrogen peroxide solution and 2.78 g of tetra-n-butylammonium chloride were mixed in 309.3 g of methanol. After the completion of the reaction, the formed precipitate was filtered out and washed with water to obtain 116.3 g of benzamide (m.p.: 130° C.) (I-4) in a yield of 96%.

EXAMPLES 36 to 51

Using several kinds of nitriles, the corresponding amides were prepared in the same manner as in Examples 32 to 35. The results are shown in Table 3.

TABLE 3

| Example No. | Raw Material | Reaction Condition | Yield |
|---|---|---|---|
| 36 | 2-phenyl-3-methylpropionitrile | Same as Example 28 | 98% |
| 37 | 3,3-diphenylpropionitrile | Same as Example 28 | 99% |
| 38 | 2-(p-tolyl)-3,3-diphenylpropionitrile | Same as Example 28 | 98% |
| 39 | 2,2-diphenylacetonitrile | Same as Example 28 | 97% |
| 40 | 2,4-dichlorobenzonitrile | Same as Example 29 | 95% |
| 41 | 2-phenyl-3-(p-tolyl)-acrylonitrile | Same as Example 29 | 96% |
| 42 | 2,3-dichloropropionitrile | Same as Example 29 | 95% |
| 43 | 2,3-diphenylpropionitrile | Same as Example 29 | 94% |
| 44 | 2-chloropropionitrile | Same as Example 30 | 94% |
| 45 | 3-hydroxypropionitrile | Same as Example 30 | 95% |
| 46 | butyronitrile | Same as Example 30 | 96% |
| 47 | 2-hydroxypropionitrile | Same as Example 30 | 95% |
| 48 | 3-phenyl-4,4-dibromobutyronitrile | Same as Example 31 | 96% |
| 49 | 2-phenoxy-3-phenylpropionitrile | Same as Example 31 | 97% |
| 50 | 2,3-bis(phenylthio)-propionitrile | Same as Example 31 | 96% |
| 51 | 3-(p-tolyl)-propionitrile | Same as Example 31 | 95% |

What is claimed is:

1. A process for preparing an amine derivative of the formula (1),

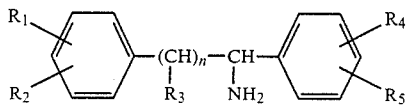

wherein $R_1$, $R_2$, $R_3$, $R_4$, and $R_5$ are independently hydrogen atom, a halogen atom, a hydroxy, trihalogenomethyl, phenyl, phenoxy or phenylthio group, or a straight or branched $C_1-C_6$ alkyl, alkenyl, alkoxyl, alkylthio, dialkylamino or alkylsulfonyl group, n is an integer of 1 to 3, provided that $R_3$s may be the same or different when n is 2 or 3, and either $R_1$ and $R_2$ or $R_4$ and $R_5$ may be bonded through the same or different atom, which comprises condensing an acetonitrile compound of the formula (4),

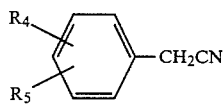

wherein $R_4$ and $R_5$ are as defined above, with a halide compound of the formula (5),

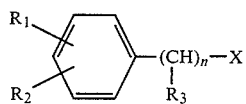

wherein $R_1$, $R_2$, $R_3$ and n are as defined above and X is a halogen atom, in the presence of a base to produce a nitrile compound of the formula (3),

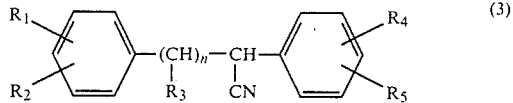

wherein $R_1$, $R_2$, $R_3$, $R_4$, $R_5$, and n are as defined above, hydrolyzing said compound of the formula (3) using as a catalyst an organic quaternary ammonium salt and/or tertiary amine in the presence of a base and hydrogen peroxide to produce an amide compound of the formula (2),

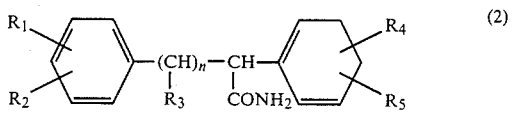

wherein $R_1$, $R_2$, $R_3$, $R_4$, $R_5$ and n are as defined above, and contacting said amide compound of the formula (2) with a halogen, an alkali metal hypohalite or an alkaline earth metal hypohalite in the presence of a base.

2. A process for preparing an amide derivative represented by the general formula (I), $$R-CONH_2 \qquad (I)$$

wherein R represents a straight or branched $C_1-C_6$ alkyl or alkenyl group, or a phenyl or aralkyl group, provided that said alkyl or alkenyl group may further have a halogen atom, or an alkoxyl, alkylthio, dialkylamino, alkylsulfonyl, phenyl, phenoxy, phenylthio or hydroxy group, and said phenyl or aralkyl group may further have an alkyl, alkenyl, alkoxyl, alkylthio, dialkylamino, alkylsulfonyl, phenyl, phenoxy, phenylthio or hydroxy group, or a halogen atom, which comprises hydrolyzing a nitrile derivative of the formula (II), $$R-CN \qquad (II)$$

wherein R is as defined above, in the presence of a base and hydrogen peroxide by using an organic quaternary ammonium salt and/or a tertiary amine as a catalyst.

* * * * *